(12) United States Patent
Kaplan

(10) Patent No.: US 8,969,411 B2
(45) Date of Patent: Mar. 3, 2015

(54) VITAMIN C COMPOSITION FOR USE IN THE PREVENTION AND TREATMENT OF STRETCH OTHER SKIN CONDITIONS AND METHODS OF USING THE SAME

(71) Applicant: David L. Kaplan, Leawood, KS (US)

(72) Inventor: David L. Kaplan, Leawood, KS (US)

(*) Notice: Subject to any disclaimer, the term of this patent is extended or adjusted under 35 U.S.C. 154(b) by 0 days.

(21) Appl. No.: 13/738,295

(22) Filed: Jan. 10, 2013

(65) Prior Publication Data

US 2013/0121981 A1    May 16, 2013

Related U.S. Application Data

(63) Continuation-in-part of application No. 12/985,098, filed on Jan. 5, 2011.

(60) Provisional application No. 61/292,365, filed on Jan. 5, 2010.

(51) Int. Cl.
| | | |
|---|---|---|
| A01N 43/08 | (2006.01) |
| A61K 31/34 | (2006.01) |
| A61K 31/375 | (2006.01) |
| A61K 8/67 | (2006.01) |
| A61Q 19/06 | (2006.01) |
| A61K 9/00 | (2006.01) |
| A61K 47/10 | (2006.01) |
| A61K 45/06 | (2006.01) |
| A61K 8/34 | (2006.01) |
| A61Q 19/00 | (2006.01) |

(52) U.S. Cl.
CPC .............. *A61K 31/375* (2013.01); *A61K 8/676* (2013.01); *A61Q 19/06* (2013.01); *A61K 9/0014* (2013.01); *A61K 47/10* (2013.01); *A61K 31/34* (2013.01); *A61K 45/06* (2013.01); *A61K 8/342* (2013.01); *A61Q 19/004* (2013.01)
USPC .......................................................... 514/474

(58) Field of Classification Search
None
See application file for complete search history.

(56) References Cited

U.S. PATENT DOCUMENTS 5,980,921 A * 11/1999 Biedermann et al. ......... 424/401
2008/0050321 A1* 2/2008 DeFilippi et al. ............... 424/59

FOREIGN PATENT DOCUMENTS

EP    2080505 A1 *  7/2009

* cited by examiner

*Primary Examiner* — Craig Ricci
*Assistant Examiner* — Jared D Barsky
(74) *Attorney, Agent, or Firm* — Lewis, Rice & Fingersh, L.C.

(57) ABSTRACT

A formulation for a stable ascorbic acid composition which, in a simplified form, is comprised of ascorbic acid in solution with a hygroscopic compound (i.e., a substance with the ability to attract water molecules from the surrounding environment through either absorption or adsorption). Also disclosed herein are methods for the production of such compounds and methods of using such compounds in the prevention, inhibition and treatment of striae gravidarum, radiation dermatitis, rhytids, lentigoes, dyschromia, sun-damage induced hyperpigmentation, cellulite, scars, purpura, skin firming, muscle, tendon and ligament improvement and repair, and hair conditions, among other skin diseases or conditions.

2 Claims, 1 Drawing Sheet

| Raw Material | Percentage of Composition |
|---|---|
| Ascorbic Acid | 5-20% |
| Hygroscopic Compound | 85-95% |
| Silicone-Based Organic Polymer | 0-3% |
| Pantothenic Acid | 0-5% |
| Tocopherol | 0-5% |
| Propylene Glycol | 0-30% |
| Ethanol | 0-20% |

VITAMIN C COMPOSITION FOR USE IN THE PREVENTION AND TREATMENT OF STRETCH OTHER SKIN CONDITIONS AND METHODS OF USING THE SAME

CROSS REFERENCE TO RELATED APPLICATION(S)

This Application is a Continuation-in-Part of U.S. Utility patent application Ser. No. 12/985,098, filed Jan. 5, 2011, which in turn claims the benefit of U.S. Provisional Patent Application Ser. No. 61/292,365, filed Jan. 5, 2010. The entire disclosure of all these documents is herein incorporated by reference.

BACKGROUND OF THE INVENTION

1. Field of the Invention

This disclosure relates to the field of vitamin C, or ascorbic acid, compositions. This disclosure also relates to the field of treatments for striae, including but not exclusive to, striae gravidarum, striae atrophicae, striae distensae, and pubertal striae; i.e., stretch marks, and the fields of treatments for radiation dermatitis, rhytids, lentigoes, dyschromia, sun-damage hyperpigmentation, cellulite, purpura and scars, amongst other skin diseases and conditions.

2. Description of Related Art

Vitamin C, or ascorbic acid, is a water-soluble micronutrient; it is an essential nutrient for humans. The vital role of ascorbic acid in human physiology flows from the essential role that ascorbate (an ion of ascorbic acid) plays in a wide range of metabolic reactions. As a strong electron donor or reducing agent, vitamin C sequentially donates two electrons from the double bond between carbons two and three. With the loss of these electrons, vitamin C is oxidized and another compound is reduced. Accordingly, vitamin C is commonly known as an antioxidant.

In humans, vitamin C is an essential cofactor for eight (8) different enzymes. Three (3) of these enzymes participate in collagen hydroxylation. Collagen is a group of naturally occurring proteins which are found in the fibrous tissues of the human body such as tendons, ligaments and skin. Ascorbic acid has been found to be an essential cofactor in the hydroxylation of proline and lysine to form hydroxyproline and hydroxylysine, amino acids necessary for the function of collagen. In fact, some studies have demonstrated that ascorbic acid can stimulate collagen synthesis preferentially without affecting non-collagen protein synthesis. See Murad S., et al., *Regulation of Collagen Synthesis by Ascorbic Acid*, Proc. Natl. Acad. Sci., 78:2870 (1981).

The same properties that make vitamin C an excellent antioxidant (its electron donor propensities) render it difficult to create a stable vitamin C formulation, as it generally rapidly oxidizes upon exposure to air. Notoriously, in the presence of water, light, air and/or high temperatures, vitamin C is not stable, generally having a half life of minutes. In fact, at higher pHs ascorbic acid increasingly becomes more unstable. Thus, historically, it has been difficult to develop stable vitamin C compositions. While stabilized topical vitamin C compositions are known; e.g., See Kaplan, et al., *A New Stabilized Ascorbic Acid Solution: Percutaneous Absorption and Effect on Relative Collagen Synthesis*, Journal of Cutaneous Aging & Cosmetic Dermatology, 1:115 (1988/89) (disclosing a 5% solution of L-ascorbic acid in a hydroalcoholic vehicle), the stability of such compositions generally have been shown only up to about one (1) month. After that time, the formulation begins to rapidly oxidize and decompose. Thus, even the "stable" topical vitamin C formulations that are currently known to those of skill in the art have a minimal shelf life and efficacy period. Furthermore, typically, when these known ascorbic acid solutions are exposed to heat, air or light; rapid degradation of the ascorbic acid solution results. This instability and potential for rapid degradation of the prior topical vitamin C formulations generally results in a high cost of manufacturing, high cost of distribution, and issues associated with storage and availability to the end consumer.

In addition to issues of stability, there also has been uncertainty with regard to the ability of the currently utilized ascorbic acid compositions to deliver pharmacologic doses of ascorbic acid percutaneously (i.e., through the skin) If ascorbic acid is to effect the connective tissue of the skin, it must penetrate the stratum corneum (i.e., the outermost layer of the epidermis of the skin) and be available to the dermal fibroblasts (i.e., the cells of the skin that synthesize collagen). While penetration of the stratum corneum with topical vitamin C solutions for delivery to the dermis (i.e., the layer of skin between the epidermis and subcutaneous tissues) are known, these solutions either suffer from a low absorption rate over time (See Kaplan, et al., *A New Stabilized Ascorbic Acid Solution: Percutaneous Absorption and Effect on Relative Collagen Synthesis*, Journal of Cutaneous Aging & Cosmetic Dermatology, 1:115 (1988/89) (Absorption progressed linearly for 72 hours and with 12.4% absorption traversing the epidermal barrier)) or instability of the topical solution itself (See Pinnell, S. R., et al., *Topical L-Ascorbic Acid: Percutaneous Absorption Studies*, Dermatol. Surg., 27(2): 137-42 (2001) (showing that daily application of an L-ascorbic acid topical solution, with a pH of 3.5 or lower, resulted in saturating skin concentrations of L-ascorbic acid at more than 20 times the control values, for four days)).

This difficulty in the art with regard to the ability to deliver pharmacologic doses of ascorbic acid percutaneously has resulted in ascorbic acid formulations with four main problems. First, these formulations often lack a sufficient concentration of ascorbic acid to be effective. In order to achieve some minimal level of stability, these formulations have low concentrations of ascorbic acid. Second, these formulations are often in suspension rather than solution, making the formulation unavailable for percutaneous absorption since it is not in a dissolved state. Third, these formulations often incorporate ascorbic acid salts that, while being more stable, do not have the same pharmacological effect as ascorbic acid on the fibroblast for collagen synthesis and do not have the same percutaneous absorption characteristics. Fourth, the rapid degradation of the ascorbic acid prevents the ascorbic acid from reaching its target in the dermal layer of the skin in a stabilized form. Thus, it is unable to exert a physiologic effect on the fibroblasts.

A stable ascorbic acid composition which could be absorbed percutaneously would have application in a number of skin diseases and conditions which are associated with a decrease or disruption in collagen synthesis. Striae gravidarum is one such condition. Striae gravidarum, otherwise known as stretch marks, is a commonly known, but poorly understood, skin disconfiguring condition that is scarring. Generally, stretch marks are characterized by a thinning of the connective tissue seronia to produce linear, atrophic-appearing skin. Stretch marks are a commonly recognized condition in both adolescent growth and pregnancy, among other situations.

Although the prevalence of stretch marks is high (among pregnant women it is reported to range between 50% and 90%) little is known about the aetiology and epidemiology of stretch marks. See Chang, Anne Lynn S, M.D., *Risk Factors*

*Associated with Striae Gravidarum*, J. Am. Acad. Dermatol., December 2004, page 881. While the development of stretch marks is commonly thought to be caused by rapid weight gain, excessive endocrine activity, growth associated with adolescence or a degree of stretch in pregnancy, there are no scientific studies that verify any of these relationships. See Chang, Anne Lynn S, M.D., *Risk Factors Associated with Striae Gravidarum*, J. Am. Acad. Dermatol., December 2004, page 881. Further, other preliminary studies have suggested that family history, personal history, and race; i.e., genetic based factors, appear predictive of the development of striae gravidarum. See Chang, Anne Lynn S, M.D., *Risk Factors Associated with Striae Gravidarum*, J. Am. Acad. Dermatol., December 2004, page 883. While genetic factors, pregnancy weight gain, the growth and hormonal changes associated with adolescence and excessive adrencortical activity are the most frequent causative factors of stretch marks, the exact aetiology is not known.

In addition to the general confusion surrounding the aetiology and epidemiology of stretch marks, dissimilar descriptions of the histological changes in striae have created confusion to those of skill in the art. Some studies hypothesize (but have yet to observe) that striae are formed by an inflammatory reaction in a very early stage in striae formation that causes destruction of collagen and elastin. As in any other damage, this inflammation is followed by regeneration of new collagen and elastin, this time oriented in the direction of stress imposed by mechanical forces, as in rapid weight gain. See Zheng, P., et al., *Anatomy of Straie*, British Journal of Dermatology, 112, 185-193 (1985). The resultant damage has been shown, in some studies, to comprise variously a thin, flattened epidermis, thinning of the dermis, fraying and separation of collagen bundles with dilatation of blood vessels, and/or separation or total absence of elastic fibers. See Lee, K. S., *Decreased Expression of Collagen and Fibronectin Genes in Straie Distensae Tissue*, Clinical and Experimental Dermatology, 19:285-288 (1994).

Notably, despite its prevalence among pregnant women and adolescents, few preventative treatments are available for stretch marks. While there are a number of creams on the market that claim to remove stretch marks once they have developed, there is no reliable evidence to support such claims. Similarly, there are only two published randomized trials of preventive topical treatments and only one of these used a placebo control. From these studies it is not clear which, if any, particular ingredient is helpful in the prevention and/or treatment of stretch marks.

Taken together, the science surrounding the cause and treatment of stretch marks is in a state of bewilderment. Accordingly, there is a need in the art for an effective topical composition for the prevention and/or treatment of striae gravidarum, especially since currently there are no commercially available proven preventive products for stretch marks.

Radiation dermatitis is another skin condition which is associated with a decrease or disruption in collagen synthesis as well as significant unintended damage to the overlying skin. Radiation dermatitis (also known as radiodermatitis) is an unintended skin reaction commonly experienced by patients receiving radiation therapy as part of their cancer treatment. This side effect, caused by radiation passing through the cells, is an unpleasant and painful condition for many cancer patients which, in some cases, may become so severe as to necessitate the interruption or cessation of radiation therapy. This, in turn, has been shown to decrease the efficacy of the radiation treatment and increase the likelihood of a cancer relapse.

Generally, radiation dermatitis manifests within a few weeks after the start of the radiotherapy. The onset of the condition varies in accordance with the radiation dose intensity, anatomic location of the radiation therapy, and the normal tissue sensitivity of individuals. This condition is experienced, to various degrees, by the majority of patients undergoing radiotherapy. While in most patients the dermatitis is mild to moderate, about 20-25% of patients experience severe reactions. Reddening of the skin, known as erythema, is an initial sign of skin dermatitis and may appear as early as the first treatment. Other symptoms also may include: epilation (i.e., hair loss), dry and wet desquamation (i.e., the shedding of the outer layers of the skin), decreased sweating, edema (i.e., swelling), ulcerations, bleeding, and skin cell death. Generally, the symptom progression has been shown to be linked with the total radiation dose, the dose per fraction, the overall treatment time, beam type and energy, and the surface area of the skin that is exposed to radiation. When the skin reaction is severe enough, it can interfere with the scheduling of the treatment regimen, which can adversely affect treatment outcomes by resulting in increased relapses of the malignancy and decreased patient survival rates.

Despite the prevalence of radiation dermatitis among individuals receiving radiation treatment, similar to striae gravidarum, there are few proven or known treatment options. While a variety of lotions, creams, and ointments have been recommended in the literature, there is a paucity of randomized trials with evidence to support the efficacy of these treatments. In fact, several trials evaluating topical agents have raised the question as to whether any product will actually prevent or promote the healing of radiation skin reactions. M. McQuestion, *Evidence-Based Skin Care Management in Radiation Therapy*, Seminars in Oncology Nursing, Vol 22, No. 3: 163-173 (2006).

Another skin condition associated with a disruption in collagen synthesis is the appearance of rhytids, commonly known as wrinkles. Wrinkles are grooves in the skin. Wrinkles form when the skin loses its strength and elasticity, or the ability to stretch as the person ages. A number of factors are thought to be the cause of wrinkles, including: loss of the strength and elasticity of the skin with age; sun damage; repeated facial movements; and the natural effects of gravity, among others. Generally, individuals with the highest risk of developing wrinkles are fair-skinned people, people who have increased sun exposure and people who have a genetic predisposition to the development of wrinkles.

Currently, there is a wide variety of modalities known to those of skill in the art that are employed to treat rhytids. These include, but are not limited too, injectable fillers, injection of *Clostridium Bitulinum* (Botox®) or similar bacteria, implants, lifts, chemical peels, dermabrasion, laser resurfacing and/or the application of retinoic acid. These known and utilized treatments can be expensive and/or invasive options for the treatment/reduction of rhytids.

Lentigo, dyschromia (i.e., alteration in color to the skin or hair) and sun-damaged induced hyperpigmentation are additional skin conditions associated with disruptions in the production of collagen. Lentigo is a benign hyperplasia of melanocytes which spreads linearly. It generally shows up as a brown to black pigmented spot on the skin. Generally, the appearance of lentigos depends on varying factors such as an individual's history of sunlight exposure and genetic predisposition, amongst others. Similar to a lentigo, hyperpigmentation is the darkening of an area of the skin or nails caused by an increase in melanin. Hyperpigmentation may be caused by sun damage, inflammation, or other skin injuries. It is associated with a number of diseases, including, but not limited to, Addison's disease, Cushing's disease, and Celiac disease, amongst other diseases and conditions.

The appearance of cellulite is another skin condition associated with collagen synthesis. Cellulite is a topographical skin change which presents itself as a modification of the topography of the skin, generally evidenced by skin dimpling and nodularity. It occurs in many women (mainly in the pelvic region, lower limbs and abdomen) and is generally caused by the herniation of subcutaneous fat within fibrous connective tissue. Cellulite is not a serious medical condition, but many, for aesthetic reasons, are interested in treatment options for the prevention or reduction of its appearance. While numerous therapies for the treatment of cellulite are available on both a prescription and a non-prescription basis, the empirical evidence for the efficacy of these techniques is limited and questionable.

Sun induced or actinic purpura is also associated with disruptions in collagen synthesis. Purpura, which is caused by bleeding underneath the skin, manifests itself as the appearance of red or purple discolorations on the skin that do not blanch with the application of pressure to the skin. Purpura associated with sun damage are the result of chronic sun exposure which produces damage to the capillaries found in the skin, resulting in easy bruising.

A stable ascorbic acid composition which could be absorbed percutaneously could also have application as a therapeutic treatment for tissues underlying the skin, including elastic tissue and the collagen in deeper tissues. For example, such a composition could be utilized for skin firming due to a loss of elastic tissue. In addition, such a composition could be utilized for strengthening ligaments and tendons which are comprised of collagen and elastic fibers in order to improve their function and prevent and treat injury to these structures. See C M, Kielty, C A, Shuttleworth, *Synthesis and Assembly of Fibrillin by Fibroblasts and Smooth Muscle Cells*, Journal of Cell Science, Vol. 106(Part 1):167-173 (September 1993).

Further, a stable ascorbic acid composition could also have application as a therapeutic treatment for a variety of hair conditions. When ascorbic acid levels in the human body are severely depleted, it results in a skin condition known as scurvy. This ascorbic acid deficiency is known to affect the hair follicle by, amongst other things, producing bruising around the hair follicle, increased skin build-up with the hair follicle or opening, and the production of abnormal hair shaft development known as "corkscrew" hairs. See M H, Kwack, et al., *l-Ascorbic Acid 2-phosphate Promotes Elongation of Hair Shafts Via the Secretion of Insulin-like Growth Factor-1 From Dermal Papilla Cells Through Phosphatidylinositol 3-kinase*," British Journal of Dermatology, 160(6):1157-62 (June 2009).

SUMMARY OF THE INVENTION

Due to these and other problems in the art, disclosed herein, among other things, is a formulation for a stable ascorbic acid composition. This composition, in a simplified form, is comprised of ascorbic acid in solution with a hygroscopic compound (i.e., a substance with the ability to attract water molecules from the surrounding environment through either absorption or adsorption). Also disclosed herein are methods for the production of such compounds and methods of using such compounds in the prevention, inhibition and treatment of striae gravidarum, radiation dermatitis, rhytids, lentigoes, dyschromia, sun-damage induced hyperpigmentation, cellulite, scars and purpura, among other skin diseases or conditions.

In one embodiment, the composition comprises: ascorbic acid in solution with a hygroscopic compound. This hygroscopic compound can be chosen from the group consisting of: glycerin, polyethylene glycol, sucrose, sorbitol, dextrose and corn syrup.

In another embodiment, the ascorbic acid composition will further comprise a silicone-based organic polymer. Possible silicone-based organic polymers include dimethicone and cylcomethicone.

In still a further embodiment, the composition can further comprise alpha lipoic acid, panthenol, pantothenic acid, tocopherol, propylene glycol and/or ethanol.

In one specific embodiment, the ascorbic acid composition comprises: 5-20% ascorbic acid; 95-85% hygroscopic compound; 0-3% silicone-based organic polymer; 0-5% pantothenic acid; 0-5% tocopherol; 0-30% propylene glycol; and 0-20% ethanol.

In another embodiment, the composition consists essentially of ascorbic acid in solution with a hygroscopic compound. In yet another embodiment, the composition consists of ascorbic acid in solution with a hygroscopic compound.

In each of the embodiments of the composition, the composition will remain stable for at least one month or, in another embodiment, for at least one year.

In addition, in one embodiment, the purity of ascorbic acid in the composition will be at least 95% after two years. In another embodiment of the composition, the purity of the ascorbic acid will be at least 95% after four years.

In one embodiment, the composition will be a topical composition.

Also disclosed herein is a composition of matter comprising: about 10% ascorbic acid in solution with about 90% of a 99% pure glycerin; and about 1% silicone-based organic polymer.

In addition to compositions, also disclosed herein is a method of producing a composition of ascorbic acid in solution with a hygroscopic compound, the method comprising: heating a hygroscopic compound to about 40-70° C.; and adding ascorbic acid to the heated hygroscopic compound to form a solution. In some embodiments of this method, the hygroscopic compound will be heated in a covered container. In other embodiments, an agitating device will be used to mix the composition.

Also disclosed herein is a method of stimulating collagen synthesis comprising: forming a composition of ascorbic acid in solution with a hygroscopic compound; and applying said composition topically to a patient's skin.

In some embodiments of this method, the composition will be topically applied to the patient for the treatment of a skin condition chosen from the group consisting of: striae gravidarum, radiation dermatitis, rhytids, lentigoes, dyschromia, sun-damage induced hyperpigmentation, cellulite, scars and pupura as well as skin firming effects on muscle, ligaments, tendons and hair growth.

BRIEF DESCRIPTION OF THE DRAWINGS

FIG. 1 provides a chart of the raw materials of an embodiment of the disclosed topical vitamin C composition.

DESCRIPTION OF PREFERRED
EMBODIMENT(S)

This disclosure is intended to teach by way of example and not by way of limitation. The present disclosure focuses on a formulation for a stable ascorbic acid composition. This composition, in a simplified form, is comprised of ascorbic acid in solution with a hygroscopic compound (i.e., a substance with the ability to attract water molecules from the surrounding environment through either absorption or adsorption). Also discussed herein are methods for the production of such compositions, along with various alternative methods of using such compounds in the prevention, inhibition and treatment of striae gravidarum, radiation dermatitis, rhytids, lentigoes, dyschromia, sun-damage induced hyperpigmentation, cellulite, scar reduction and purpura, among other skin diseases.

In one embodiment of the disclosed ascorbic acid composition in solution, the hygroscopic compound comprises: glycerin, polyethylene glycol, sucrose, sorbitol, dextrose, corn syrup and combinations thereof. However, in no way is this group intended to be exhaustive, as this disclosure contemplates the use of any hygroscopic compound, known now or in the future, to those of skill in the art which has the ability to attract water molecules from the surrounding environment through either absorption or adsorption. Generally, any means for attracting water molecules from the environment through absorption or absorption in which ascorbic acid can be placed in solution is contemplated in this disclosure. In one embodiment, the composition will consist essentially of ascorbic acid in solution with a hygroscopic compound such as glycerin, polyethylene glycol, sucrose, sorbitol, dextrose and/or corn syrup. This composition may potentially be mixed with other compounds which may or may not provide additional skin benefits. In another embodiment, the composition consists of ascorbic acid in solution with a hygroscopic compound, which is suitable for the stimulation of collagen synthesis. In one embodiment it is contemplated that a glycerin of a high purity, e.g., 99%, will be utilized as the hygroscopic compound in the composition.

While the invention is not intended to be limited to any physiological effect of the modality of the stable topical ascorbic acid composition, it is hypothesized that one explanation for the stability of this ascorbic acid composition (compared to other ascorbic acid compositions utilized in the art) is that the water attraction qualities of the hygroscopic compound base impede the reduction of the ascorbic acid mixed therewith, thereby reducing the volatility of the ascorbic acid. Stated differently, the hygroscopic nature of the glycerin (or other hygroscopic compound in which the ascorbic acid is in solution) acts to pull any water away from the ascorbic acid, thereby allowing it to be stabilized without being degraded.

In more complex embodiments of the disclosed composition, the composition is further comprised of a silicone-based organic polymer, in addition to the ascorbic acid in solution with the hygroscopic compound. Contemplated silicone-based organic polymers include, but are not limited to, dimethicone and cylcomethicone. However, any silicone-based organic polymer known to those of skill in the art is contemplated in this disclosure. Generally, these silicone-based organic polymers are added to the composition for the viscoelastic properties (i.e., viscous and elastic characteristics) they impart, which, while not having an effect on collagen hydroxylation, do have an effect on certain properties of the topical composition such as smooth application. These silicone-based polymers are also added, in some embodiments, for their ability to increase the aesthetic performance of the formulation. Generally, glycerin alone does not result in a cosmetically elegant formulation. The addition of the silicone polymers changes the rheologic qualities of the formulation to increase the aesthetic pleasure of the formulation, thereby increasing the likelihood of use by a given individual. See. Forster, et al., *Rheology of siloxane-stabilized water in silicone emulsions*, Int. J. Cosmet. Sci., 19(4): 173-91 (August 1997) (showing use of silicone copolymers in personal care products can improve the aesthetic performance of formulations). Although sometimes glycerin alone does not result, in some cases, in a cosmetically elegant formulation, compositions comprised of just a hygroscopic compound, like glycerin, and ascorbic acid are contemplated herein.

In some embodiments, the silicone-based organic polymers will comprise only a small percentage of the overall composition. An example of the percentages of composition of one embodiment of the disclosed composition, wherein the components are ascorbic acid, glycerin and a silicone-based organic polymer, is as follows: about 10% ascorbic acid in about 90% of a 99% pure glycerin with about 0-1% of a silicone-based organic polymer.

In another embodiment, the composition is comprised of additional ingredients besides a silicone-based organic polymer. Contemplated additional ingredients include, but are not limited to, alpha lipoic acid, panthenol, pantothenic acid, tocopherol and its derivatives, ethanol and propylene glycol. Generally, the panthenol and propylene glycol are added to the composition for their moisturizing properties. Pantothenic acid, i.e., vitamin $B_5$, is included because of its position as an essential nutrient required to sustain life. Ethanol is included because of its ability to increase the stability and absorption of the solution, in addition to its ability to improve the cosmetic elegance of the composition. Tocopherol and its derivatives are included in some embodiments of the formulation for generally two reasons. One, their antioxidant properties. Two, tocopherol and its derivatives are commonly used as components to stabilized formulations that have high potential for oxidative degradation. Accordingly, although not necessary for stabilization of the composition disclosed herein, tocopherol and its derivatives can be added to the disclosed formulation for their supplementary stabilization qualities. Alpha lipoic acid may be included to enhance the activity of collagen production by fibroblasts through transforming growth factor beta.

In alternative or further embodiments, supplemental minerals also may be included. Suitable minerals may include one or more minerals or mineral sources. Non-limiting examples of minerals include: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

The compositions also may optionally comprise additional vitamin compositions. The vitamins may be fat-soluble or water soluble vitamins. Suitable vitamins include but are not limited to: vitamin A, vitamin E, vitamin B12, vitamin K, riboflavin, niacin, vitamin D, vitamin B6, folic acid, pyridoxine, thiamine, and biotin. The form of the vitamin may include salts of the vitamin, derivatives of the vitamin, compounds having the same or similar activity of a vitamin, and metabolites of a vitamin.

The composition also may comprise at least one excipient. Non-limiting examples of suitable excipients include: a preservative, a stabilizer, a binder, a compaction agent, a lubricant, a dispersion enhancer, a coloring agent, and combinations of any of these agents. The excipient also may comprise a preservative. Suitable examples of preservatives include other antioxidants and antimicrobials, such as parabens, chlorobutanol, or phenol.

In an alternative or further embodiment, the excipient may be a binder. Suitable binders include: starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In an alternative or further embodiment, the excipient may be a lubricant. Suitable non-limiting examples of lubricants include: magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient also may be a dispersion enhancer. Suitable dispersants may include: starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Generally, contemplated ranges for certain components of the composition in various different embodiments are as follows: about 5-20% ascorbic acid; about 0-3% of a silicone-based organic polymer; about 0-5% alpha lipoic acid; about 0-5% pantothenic acid; about 0-5% tocopherol and its derivatives; about 0-20% ethanol; and about 0-30% propylene glycol in about 85-90% hygroscopic compound. See FIG. 1. In another embodiment of the composition where the composition is comprised of ascorbic acid in a hygroscopic compound with a silicone-based organic polymer, contemplated ranges for certain components of the composition are: about 5-20% ascorbic acid in about 80-95% hydroscopic compound with about 0-20% silicone-based organic polymers. Notably, however, in no way is this listing of ranges intended to be exhaustive, as other ranges could be contemplated in additional embodiments of the composition.

Generally, the stable topical ascorbic acid composition described herein may take any form known to those of skill in the art now or in the future for topical solutions including, but not limited to, a solution, a lotion, a shake lotion, a cream, an ointment, a gel, a foam, and/or a transdermal patch. While this application generally discusses the stable ascorbic acid solution as a topical composition, alternative methods of delivery of compositions are also contemplated. The compositions disclosed herein may be formulated into a variety of forms and administered by a number of different means.

Due, in part, to the rapid oxidation of ascorbic acid upon exposure to heat, air and/or moisture, methods and/or processes for the creation of ascorbic acid compositions have traditionally had low concentrations. For example, according to the Merck Index (i.e., an industry-wide recognized encyclopedia of chemicals, drugs and biologicals), the solubility of ascorbic acid in glycerol is one (1) gram per one hundred (100) mL of glycerol, a solubility which would result in a final concentration of one percent (1%). See *Merck Index, Twelfth Addition*, Merck & Co., Inc., pp 867-868 (1996). The application of heat and other methodologies which are generally employed to create a solution with higher solubility concentrations where traditionally not seen as an option for the creation of ascorbic acid compositions because of the role heat plays in the oxidation and rapid degradation of ascorbic acid.

This traditional limitation in the concentrations of ascorbic acid solutions is overcome in the processes and methods for the production of the stable topical ascorbic acid solutions described herein by the gentle heating of the hygroscopic compound base while the ascorbic acid is added thereto to create a solution. While not intending to be limited to any particular theory of occurrence, this heating is believed to be possible because of the water attraction qualities of the hygroscopic base, which impede the reduction of the ascorbic acid mixed therewith, reducing the volatility of the ascorbic acid. The water attraction properties of the hygroscopic base not only protect the composition from degradation over time caused by exposure to air and moisture, but also, surprisingly, protect the ascorbic acid from degradation upon exposure to heat in certain identifiable ranges.

By this method and process, supersaturated compositions of up to 20% solubility can be achieved without oxidation or degradation of the ascorbic acid. As used in this application, degradation means oxidation of the ascorbic acid of the composition to a point at which the composition no longer contains a pharmacologically effective quantity of ascorbic acid to stimulate collagen synthesis.

In one embodiment of the method and process, the ascorbic acid is added to the hygroscopic compound as it is gently heated to a temperature between about 40 to 70 degrees Celcius in a covered container (the container is generally only covered; an airtight vacuum or an oxygen-free seal is not required but can be used in alternate embodiments) using a stirring rod or other mixing or agitating device known to those of skill in the art. Methods and processes for the creation of ascorbic acid solutions in this manner; i.e., via "gentle heating," are not known to have been reported in the art. In fact, previous studies and reports in the art teach away from such a method or process for the creation of an ascorbic acid solution, as these studies and reports suggest that ascorbic acid will rapidly degrade upon exposure to air and upon heating. However, as noted further above, the hygroscopic properties of the composition (as a result of the hygroscopic base) are believed to protect the ascorbic acid from oxidizing under conditions that would normally produce degradation in the ascorbic acid compositions previously known in the art. Further, surprisingly, the hygroscopic properties of the composition (imparted to the composition by the hygroscopic base) have been shown to protect the ascorbic acid from degradation at raised temperatures between about 40 to 70 degrees Celsius for a substantial period of time, in some tests up to seven (7) days.

The advantages of the disclosed topical ascorbic acid composition are generally three-fold. First, the disclosed composition is exceedingly stable in comparison to currently known ascorbic acid compositions. Preliminary testing has shown the disclosed composition to be stable for at least up to one (1) year, even after the bottle has been exposed to air.

The extreme stability of the disclosed ascorbic acid compositions is demonstrated in the test results provided in Table 1. Similar to degradation, the terms "stability" or "stable," as used in this application, are defined in terms of the pharmacologically effective amount of ascorbic acid contained in the composition—the composition is not stable when it no longer contains a therapeutically effective amount of ascorbic acid to be absorbed percutaneously and to stimulate collagen production.

To test the stability of the disclosed ascorbic acid compositions, three different compositions were purposefully aged at room temperature for varying periods of time. The compositions were then tested to determine the purity of the ascorbic acid in the aged composition; i.e., to determine the degree to which the ascorbic acid had oxidized over time.

TABLE 1

| Composition | Age of Composition When Tested | Amount of Ascorbic Acid in Original Solution | Amount of Ascorbic Acid in Aged Solution | Purity of Ascorbic Acid in Aged Solution | pH of Ascorbic Acid in Aged Solution |
|---|---|---|---|---|---|
| Ascorbic Acid in 10% Glycerin | ~12 months | 100 mg/mL | 97.32 mg/mL | 97.32% | 1.91 |
| Ascorbic Acid in 10% Glycerin | ~52 months | 100 mg/mL | 96.78 mg/mL | 96.78% | 2.06 |
| Ascorbic Acid in 15% Glycerin | ~52 months | 150 mg/mL | 149.84 mg/mL | 99.89% | 2.10 |

As seen in Table 1, stability of the solution was maintained (with a purity of ascorbic acid of 96.78% for a 10% solution and 99.89% for a 15% solution) even for a composition aged about 52 months (more than four years) at room temperature. Again, purity of ascorbic acid at these levels in compositions aged for such long durations of time are not known to have been previously reported in the art. Accordingly, this application contemplates ascorbic acid compositions wherein the purity of the ascorbic acid is at least 90%, 95%, 97% or 99% after at least four (4) years of storage. This application also contemplates ascorbic acid compositions wherein the purity of the ascorbic acid is at least 90%, 95%, 97% or 99% after at least two (2) years of storage.

Second, heating of the disclosed composition of ascorbic acid in a solution of glycerin (or other hydroscopic compound), even when exposed to air, does not result in degradation of the ascorbic acid in the composition. In fact, testing has shown that the disclosed composition can be "gently heated" at temperatures of about 40 to 70 degrees Celsius for up to seven (7) days without degradation of the ascorbic acid. This is in stark contrast to the ascorbic acid compositions of the prior art, in which the ascorbic acid would rapidly degrade in the presence of heat and/or air while in solution.

Third, it is commonly understood in the art that ascorbic acid compositions with a pH of 5 or higher are exceedingly unstable—the higher the pH of the ascorbic acid composition, the more rapidly it will oxidize. However, previously, topical ascorbic acid compositions with a pH of about 2.5 or lower were generally not recognized as possibilities because previously known topical ascorbic acid compositions with pHs at these levels resulted in skin irritation issues and were not tolerated topically. The disclosed ascorbic acid composition solves both of these problems. The hygroscopic base of the disclosed composition, in addition to protecting the ascorbic acid from heat and air associated degradation, is also a unique solvent because it allows for a lower pH. As demonstrated in Table 1, the pH of the disclosed composition is about 2.5 or lower or about 2.0 or lower across a variety of aged compositions. This lower pH is important because stability is directly correlated with the pH of ascorbic acid compositions; the lower the pH, the more stable the composition. Further, even though it has a lower pH, the disclosed composition does not cause skin irritation when applied topically.

One contemplated use for the stable topical ascorbic acid compositions disclosed herein is for the prevention, inhibition, and/or treatment of striae gravidarum. Without any intention to be limited by any theory or mechanism of operation, the hypotheses in the art as to the histological changes in striae support one of the working theories of the present application; i.e., that the mechanical forces on the skin during pregnancy and puberty (among other conditions commonly associated with the appearance of striae) result in the clinical changes referred to as "stretch marks," and that a stabilized formulation of ascorbic acid, if properly formulated, would be able to have a pharmacologic effect on the fibroblasts, augmenting the production of normal collagen and elastin of sufficient quantity and quality to prevent formation of stretch marks and/or reduce the appearance of stretch marks. Ascorbic acid could also possibly contribute an anti-inflammatory effect, as well as an anti-oxidative effect, on the fibroblasts.

In one embodiment of a method of using the stable topical ascorbic acid composition disclosed herein for the prevention of striae gravidarum, the topical ascorbic acid composition is applied to the body surfaces of a pregnant woman that are common sites for the appearance of striae gravidarum; e.g., breasts, hips, thighs, and abdomen. Frequency of the application can vary, from several applications a day to once every few days, to once every week. Similarly, the duration of the application can vary from a quick application until absorbed into the skin to a longer application associated with massage of the treated skin area. Further, the timing of the application can vary. For example, in one embodiment, treatment with the stable topical ascorbic acid composition described herein will commence at the beginning of the pregnancy, acting as a preventative treatment to the appearance and onset of striae. In contrast, in other embodiments, the treatment may begin in the middle of the pregnancy term, at the end of the pregnancy term, or after the pregnancy term—when striae gravidarum have already appeared—in order to diminish and/or eliminate the size of the skin legions. Notably, none of these factors (i.e., frequency, duration, timing and type of application) should be viewed as determinative or limiting to the disclosed treatment modality.

In addition to use for the treatment of striae gravidarum in pregnant women, it is also contemplated that the disclosed stable topical ascorbic acid composition will be used for the treatment of pubertal striae in adolescent individuals, individuals with Cushing's disease, steroid users, and other groups known now, or in the future, to be susceptible to the appearance of striae gravidarum. Again, the frequency, duration, timing, and the type of application of the stable ascorbic acid composition described herein to these groups is not determinative or limiting, as any application method known to those of skill in the art is contemplated in these target groups. Further, it should be noted that it is contemplated that the stable topical ascorbic acid composition disclosed herein can be utilized alone, or in combination with other treatments known now or in the future for the treatment and/or prevention of striae gravidarum.

The hypothesized ability of a stabilized formulation of ascorbic acid, if properly formulated, to have a pharmacologic effect on the dermal fibroblasts, augmenting the production of normal collagen and elastin of sufficient quantity and quality to stimulate collagen synthesis, has application in other skin conditions or diseases associated with a disruption in collagen hydroxylation. One such condition is radiation dermatitis. In one embodiment of the disclosed method for treatment of radiation dermatitis with the stable topical ascorbic acid composition disclosed herein, the composition is applied, via any method known to those of skill in the art for application of a topical formulation, to the skin of an individual undergoing radiation treatment prior to the individual's first treatment. Any radiation treatment associated with the onset of radiation dermatitis, now or in the future, is contemplated as a treatment population for the disclosed topical ascorbic acid composition. In another embodiment of the disclosed method for treatment of radiation dermatitis with the stable topical ascorbic acid composition disclosed herein, the stable topical ascorbic acid composition is applied during radiation treatment, preferably at the onset or within one to four weeks of treatment when early radiation skin reactions generally begin to occur. In still other embodiments, the topical ascorbic acid composition described herein will be applied after the appearance of radiation skin reactions.

Akin to the methods for treating striae gravidarum with the topical ascorbic acid composition, the frequency, duration, timing and type of application of the stable ascorbic acid composition described herein are not determinative or limiting, as any frequency, duration, timing or type of application known now, or in the future, to those of skill in the art is contemplated. Further, it is contemplated that the topical ascorbic acid composition described herein may be used alone, or in combination with other treatments known to those of skill in the art for the treatment and/or prevention of radiation dermatitis, such as, but not limited to: washing, aloe vera, biafins (e.g., trolamine), hyaluronic acid cream, corticosteroids, sucralfate, barrier films, antimicrobials, dressings, and hydrophilic dressings.

In addition to use in methods for the treatment/prevention of striae gravidarum and radiation dermatitis, it is also contemplated that the stable topical ascorbic acid composition disclosed herein may be utilized in a method for the treatment and/or prevention of any other skin disease or affliction associated with the break-down, degeneration, or disturbance of the collagen framework in human or other animal skin. Such skin conditions include, but are not limited to, rhytids (skin wrinkles), lentigoes, dyschromia, sun-damaged induced hyperpigmentation, cellulite, scars and sun induced or actinic pupura. Again, the frequency, duration, timing and type of application of the stable ascorbic acid composition described herein in these methods are not determinative or limiting. Further, the stable ascorbic acid solution of this disclosure can be used alone or in combination with other treatments for the treatment and/or prevention of these diseases or conditions.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A solution consisting of:
   between 85-90% by weight of glycerin solvent;
   between 5-15% by weight of an ascorbic acid solute, said ascorbic acid solute solubilized in said glycerin solvent;
   greater than 0% and less than 3% by weight of a silicone-based organic polymer;
   greater than 0% and less than 5% by weight of an alpha lipoic acid;
   greater than 0% and less than 5% by weight of a pantothenic acid;
   greater than 0% and less than 5% by weight of a tocopherol or a derivative thereof;
   greater than 0% and less than 10% by weight of an ethanol; and
   greater than 0% and less than 10% by weight of a propylene glycol.

2. A solution consisting of:
   between 85-90% by weight of glycerin solvent;
   between 5-15% by weight of an ascorbic acid solute, said ascorbic acid solute solubilized in said glycerin solvent;
   greater than 0% and less than 3% by weight of a silicone-based organic polymer;
   greater than 0% and less than 5% by weight of an alpha lipoic acid;
   greater than 0% and less than 10% by weight of a panthenol;
   greater than 0% and less than 5% by weight of a tocopherol or a derivative thereof;
   greater than 0% and less than 10% by weight of an ethanol; and
   greater than 0% and less than 10% by weight of a propylene glycol.

* * * * *